United States Patent [19]

Mouchawar

[11] Patent Number: 5,601,608
[45] Date of Patent: Feb. 11, 1997

[54] METHODS AND APPARATUS FOR APPLYING CHARGE-BALANCED ANTIARRHYTHMIA SHOCKS

[75] Inventor: Gabriel Mouchawar, Newhall, Calif.

[73] Assignee: Pacesetter, Inc., Sylmar, Calif.

[21] Appl. No.: 382,766

[22] Filed: Feb. 2, 1995

[51] Int. Cl.$^6$ ........................................................ A61N 1/39
[52] U.S. Cl. ................................... 607/5; 607/13; 607/74
[58] Field of Search ................................ 607/13, 5, 74, 607/7, 4

[56] References Cited

U.S. PATENT DOCUMENTS

| 3,835,865 | 9/1974 | Bowers | 607/13 |
|---|---|---|---|
| 4,373,531 | 2/1983 | Wittkampf et al. | 607/13 |
| 4,543,956 | 10/1985 | Herscovici | 607/13 |
| 4,592,359 | 6/1986 | Galbraith | 128/419 R |
| 4,608,985 | 9/1986 | Crish et al. | 128/419 R |
| 4,821,723 | 4/1989 | Baker, Jr. et al. | 128/419 D |
| 4,821,724 | 4/1989 | Whigham et al. | 128/419 P |
| 5,083,562 | 1/1992 | de Coriolis et al. | 128/419 D |
| 5,165,403 | 11/1992 | Mehra | 607/122 |
| 5,172,690 | 12/1992 | Nappholz et al. | 607/13 |
| 5,179,946 | 1/1993 | Weiss | 128/419 D |
| 5,184,615 | 2/1993 | Nappholz et al. | 128/419 PG |
| 5,184,616 | 2/1993 | Weiss | 128/419 |
| 5,269,319 | 12/1993 | Schulte et al. | 607/123 |

Primary Examiner—William E. Kamm
Assistant Examiner—Kennedy J. Schaetzle
Attorney, Agent, or Firm—Harold C. Schloss

[57] ABSTRACT

Methods and apparatus are provided for generating multiphasic charge-balanced cardioversion and defibrillation shocks to apply to a patient's heart to terminate episodes of arrhythmia such as tachycardia and fibrillation. The time-integrated positive shock phase current equals the time-integrated negative shock phase current. The use of charge-balanced shocks has been determined to significantly reduce the effects of post shock block that result when conventional shocks are applied to the heart.

13 Claims, 5 Drawing Sheets

METHODS AND APPARATUS FOR APPLYING CHARGE-BALANCED ANTIARRHYTHMIA SHOCKS

BACKGROUND OF THE INVENTION

This invention relates to methods and apparatus for applying cardioversion and defibrillation shocks to a patient's heart, and more particularly, to methods and apparatus for applying charge-balanced shocks (waveforms) to the heart.

Cardiac stimulating devices such as pacemakers and cardioverter-defibrillators are well known. Typically, cardiac stimulating devices contain sensing circuitry for monitoring the various heartbeat signals produced by a patient's heart. Cardiac stimulating devices with sensing circuitry can analyze the patient's heartbeat signals to determine when and at what energy level any electrical pulses should be applied to the heart.

Some cardiac stimulating devices can determine whether the patient is suffering from an arrhythmia such an episode of tachycardia or a fibrillation event. When an arrhythmia is detected, a cardiac stimulating devices may attempt to terminate the arrhythmia by applying electrical pulses to the patient's heart. These pulses may be in the form of high energy cardioversion or defibrillation shocks. Cardioversion pulses have energies in the range of about 2–5 J. Typical defibrillation shocks have energies in the range of about 30–40 J.

Shocks are applied to the patient's heart via leads and electrodes. It is well known that when current is passed through an electrode submerged in an electrolyte such as interstitial fluid or blood, the electrode/electrolyte interface polarizes. The shock-induced polarization produces a voltage rise that can obscure the patient's heartbeat signals. This effect, which is commonly known as "post shock block," is most dramatic in systems in which the electrodes used to apply the shock are adjacent to, or the same as, the electrodes used to sense the heartbeat signals.

As a result of post shock block, whenever a cardioversion or defibrillation shock is applied to the heart it becomes impossible for the sensing circuitry to detect the heartbeat signals until the blocking voltage decays. During the 5–30 second period before the shock induced voltage decays, the cardiac stimulating device is not able to monitor the patient's condition. The cardiac stimulating device is therefore unable to determine whether or not the shock that was just applied was successful at terminating the arrhythmia. A failure to successfully terminate a tachycardia or a fibrillation might require that a more aggressive therapy be applied in a further attempt to terminate the arrhythmia. Unfortunately, due to post shock block, it is not possible to determine the appropriate course of action until the polarization voltage induced by the shock decays.

What is therefore needed is a way in which to reduce the effects of post shock block.

SUMMARY OF THE INVENTION

In accordance with the principles of the present invention, methods and apparatus are provided for applying charge-balanced cardioversion and defibrillation shocks to a patient's heart.

When conventional cardioversion and defibrillation shocks are applied to the heart to terminate arrhythmia episodes, the electrode/electrolyte interface used to apply such shocks becomes polarized. The polarized interface creates an effect known as post shock block, which obscures heartbeat signals from the sensing circuitry used to monitor these signals. Charge-balanced shocks have at least one positive shock phase and at least one negative shock phase. The sum of the time-integrated currents of the positive phases of the shock is equal to the sum of the time-integrated currents of the negative phases of the shock. As a result, the charge delivered to the electrode/electrolyte interface during the positive phases is balanced by the charge removed during the negative phases. Shocks of this type do not polarize the interface as conventional shocks, thus significantly reducing the effects of post shock block.

Two particularly suitable charge-balanced shock waveforms are the biphasic shock waveform and the triphasic shock waveform. The biphasic charge-balanced shock waveform has a single positive shock phase and a single negative shock phase. The time-integrated current of the positive shock phase is equal to the time-integrated current of the negative shock phase. When the charge-balanced biphasic shock waveform is applied to the patient's heart to terminate an arrhythmia, the sensing electrode/electrolyte interface is polarized less than when a conventional shock waveform is used, thereby reducing the effects of post shock block.

A suitable triphasic charge-balanced shock waveform has either two positive shock phases and a single negative shock phase or two negative phases and a single positive phase. The sum of the time-integrated currents of the two phases is equal to the time-integrated current of the shock phase with the opposite polarity. When the charge-balanced triphasic shock waveform is applied to the patient's heart to terminate an arrhythmia, the sensing electrode/electrolyte interface is polarized less than with a conventional shock, so that the effects of post shock block are significantly reduced. The defibrillation efficacy of biphasic, and particularly triphasic, charge-balanced shocks is comparable to or superior to that of conventional shocks.

Charge-balanced shocks can be applied to the patient's heart using any suitable lead arrangement. For example, a bipolar or a tripolar lead can be used. A suitable storage capacitor within a cardiac stimulating device can be charged when it is desired to apply the charge-balanced shock. Switching circuitry is preferably used to alternately apply the positive and negative shock phases to the heart by discharging the capacitor through the blood and heart tissue of the patient. Control circuitry ensures that the durations of the positive and negative shock phases are such that the total magnitude of the time-integrated current of the positive phases is equal to that of the negative phases.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF PREFERRED EMBODIMENTS

Cardiac stimulating devices such as pacemakers and cardioverter-defibrillators are well known. A variety of devices are presently available that apply electrical pulses to a patient's heart in order to maintain a healthy heart rhythm. Some cardiac stimulating devices simply apply pacing pulses to the patient's heart at regular predetermined intervals. More typically, cardiac stimulating devices contain sensing circuitry for monitoring the various heartbeat signals produced by a patient's heart. Cardiac stimulating devices with sensing circuitry can analyze the patient's heartbeat signals to determine when and at what energy level any electrical pulses should be applied to the heart.

Some cardiac stimulating devices can determine whether the patient is suffering from an arrhythmia such an episode of tachycardia (a condition in which the heart beats too quickly) or a fibrillation event (a condition in which the heart quivers chaotically). When an arrhythmia is detected, appropriate corrective therapies can be applied to the heart. Some cardiac stimulating devices attempt to terminate tachycardia episodes by applying bursts of fairly weak electrical pulses to the patient's heart. Other cardiac stimulating devices can apply high energy shocks to the heart. For example, some devices contain cardioversion circuitry, which allows individual pulses having energies in the range of about 2–5 J to be applied to the heart to terminate an arrhythmia. Cardiac stimulating devices with defibrillation capabilities can apply still higher energy pulses to terminate heart fibrillation. Typical defibrillation shocks have energies in the range of about 30–40 J.

Shocks are applied to the patient's heart using leads containing various electrodes. It is well known that when current is passed (e.g., defibrillation shock) through an electrode submerged in an electrolyte such as interstitial fluid or blood, the electrode/electrolyte interface polarizes (i.e., it will maintain a potential after the current flow stops). The shock-induced polarization produces a voltage rise that can obscure the patient's heartbeat signals. This effect, which is commonly known as "post shock block," is most dramatic in systems in which the electrodes used to apply the shock are adjacent to the electrodes used to sense the heartbeat signals.

As a result of post shock block, whenever a cardioversion or defibrillation shock is applied to the heart it becomes impossible for the sensing circuitry to detect the heartbeat signals until the blocking voltage decays. However, about 5–30 seconds may elapse before the voltage induced by the shock decays sufficiently to allow the sensing circuitry to detect the patient's heartbeat signals. During this period, the cardiac stimulating device is not able to monitor the patient's condition. The cardiac stimulating device is therefore unable to determine whether or not the shock that was just applied was successful at terminating the arrhythmia.

A successful termination of a tachycardia or fibrillation episode might require that no pacing pulses be applied, or might require that pacing pulses be applied only if the patient's heart does not beat on its own. A failure to successfully terminate a tachycardia or a fibrillation might require that a more aggressive therapy be applied in a further attempt to terminate the arrhythmia. But because of post shock block, it is not possible to determine the appropriate course of action until the polarization voltage induced by the shock decays.

One approach for alleviating the effects of post shock block is to locate the electrodes used to apply cardioversion and defibrillation shocks ("the shock electrodes") at a position remote from the electrodes that are used to sense the heartbeat signals ("the sense electrodes"). Although this is theoretically possible, in practice a more compact lead arrangement having at least one of the shock electrodes on the same lead as a sense electrode is often preferred. Two commonly used lead arrangements are the bipolar lead and the tripolar lead.

Figure 1:
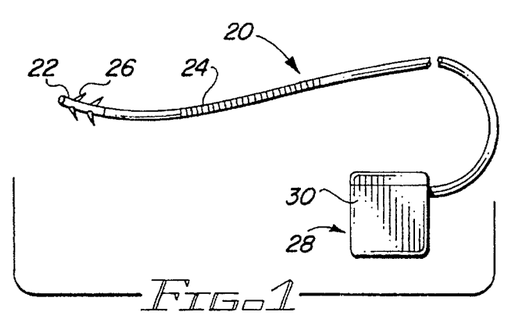
FIG. 1 is a perspective view of a bipolar lead arrangement connected to a cardiac stimulating device.

A typical bipolar lead 20 is shown in FIG. 1. The bipolar lead 20 has two electrodes: a tip electrode 22 and a coil electrode 24. The bipolar lead 20 is connected to a cardiac stimulating device 28. The cardiac stimulating device 28 contains circuitry for monitoring the patient's heartbeat signals and for applying high energy pulses to the heart in response to detected arrhythmias. The cardiac stimulating device 28 is typically also capable of providing pacing pulses to the heart when needed.

In operation, the bipolar lead 20 is surgically implanted in a patient's heart (e.g., in the patient's right ventricle). The tip electrode 22 typically is capable of being attached to the heart wall. For example, the tip electrode 22 may have tines 26, which hold the tip into place or the tip electrode 22 may have a portion that allows it to be screwed into place. The patient's heartbeat signals are monitored by measuring the voltage between the tip electrode 22 and a coil electrode 24 using the sensing circuitry contained within the cardiac stimulating device 28. Thus, the sense electrodes in a bipolar lead are the tip electrode 22 and the coil electrode 24.

If the cardiac stimulating device 28 has a pacing capability, pacing pulses can be supplied to the heart via the tip electrode 22 and the coil electrode 24. Because the coil electrode is much larger than the tip electrode 22, the current density is greatest near the tip electrode 22, so that most of the electrical stimulation of the pacing pulse is applied to the heart in the vicinity of the tip electrode 22. In this configuration, the coil electrode 24 is known as the indifferent electrode for pacing and sensing.

High energy antiarrhythmia shocks are applied to the heart using the coil electrode 24 and a can electrode 30 (the metallic housing of the cardiac stimulating device 28). Thus, for a typical bipolar lead arrangement, the two shock electrodes are formed by the coil electrode 24 (also the indifferent pacing and sensing electrode) and the can electrode 30. Because the can electrode 30 is much larger than the coil electrode 24 the can 30 is the indifferent shock electrode.

Figure 2:
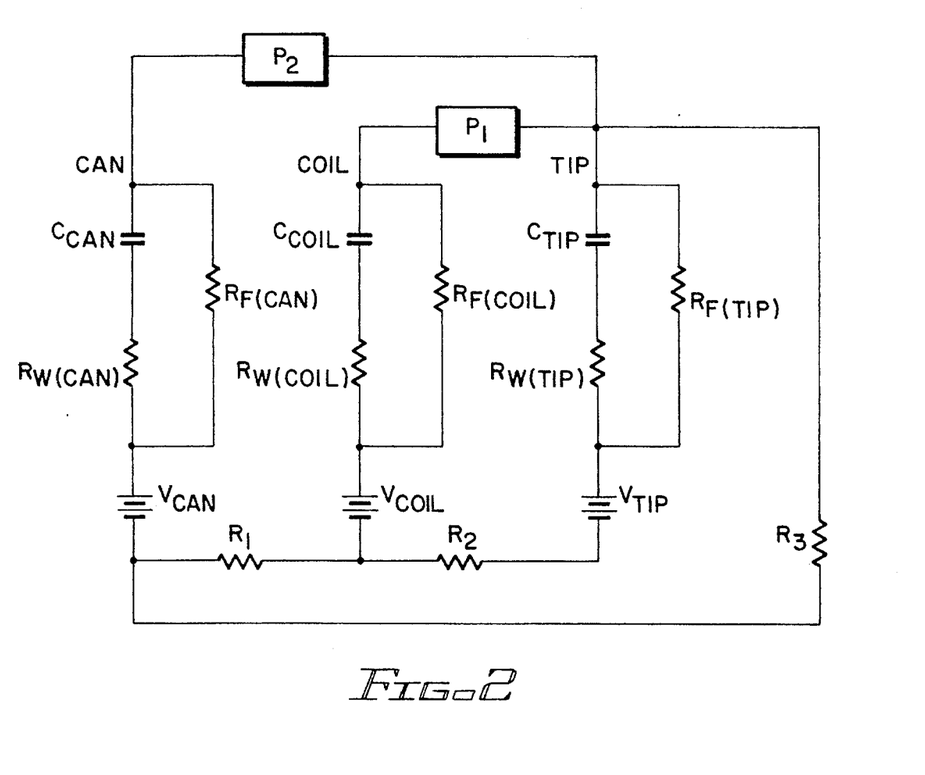
FIG. 2 is a schematic diagram illustrating the effective circuit of the can, coil, and tip electrodes of FIG. 1 in contact with the blood and tissue of a heart.

When the bipolar lead configuration of FIG. 1 is used, shocks applied with the coil electrode 24 and the can electrode 30 polarize the electrode/electrolyte interfaces of these two electrodes. The equivalent circuit of the arrangement of FIG. 1 is shown in FIG. 2. As is well known, in cardiac stimulating devices the interface between the blood and heart tissue of the patient and each electrode can be modelled as a capacitance (the Warburg capacitance) in series with a resistance (the Warburg resistance) both of which are in parallel with a resistance known as the Faradic resistance. As shown in FIG. 2, for the lead configuration of FIG. 1, the Warburg capacitances of the can 30, the coil 24, and the tip 22 are $C_{CAN}$, $C_{COIL}$, and $C_{TIP}$. The Warburg resistances for the FIG. 1 system are $R_{W(CAN)}$, $R_{W(COIL)}$, and $R_{W(TIP)}$ and the Faradic resistances are $R_{F(CAN)}$, $R_{F(COIL)}$, and $R_{F(TIP)}$. The voltages $V_{CAN}$, $V_{COIL}$, and $V_{TIP}$ are the half-cell potentials that develop between the respective electrodes and the surrounding blood and heart tissue. The resistances $R_1$, $R_2$ and $R_3$ represent the bulk resistance of the blood and tissue between the electrodes.

When a shock is applied between the can electrode 30 and the coil electrode 24 (FIG. 1), the capacitances $C_{CAN}$, $C_{COIL}$, are charged by the current that flows between these electrodes through the blood and heart tissue. The capacitance $C_{TIP}$ is charged by leakage currents in the sensing circuitry due to the defibrillation shock. Illustrative leakage current paths between CAN, COIL and TIP, that pass through $C_{TIP}$, $P_1$ and $P_2$ are shown in FIG. 2. Leakage elements $P_1$ $_{and\ P2}$ are parasitic pathways within the device's electronics and can be resistive, capacitive and/or nonlinear elements, such as zener diodes, used to protect the sensing electronics against transient high voltages. The voltages on capacitors $C_{COIL}$ and $C_{TIP}$ cause the post shock block effect. The various capacitances and resistances of FIG. 2 continually fluctuate, so it is not possible to determine what the voltages induced on the capacitors will be when a given shock is applied to the heart. As a result, when the sensing circuitry in the cardiac stimulating device 28 (FIG. 1) attempts to monitor the patient's heartbeat by measuring the voltage difference between TIP and COIL, the voltage difference on $C_{COIL}$ and $C_{TIP}$ obscure the heartbeat signals. Although capacitors $C_{CAN}$, $C_{COIL}$, and $C_{TIP}$ eventually discharge through the various resistances, until the capacitors discharge sufficiently to reduce the voltages on the capacitors below the level of the patient's heartbeat signals, the cardiac stimulating device 28 (FIG. 1) is unable to monitor the patient's condition.

Figure 3:
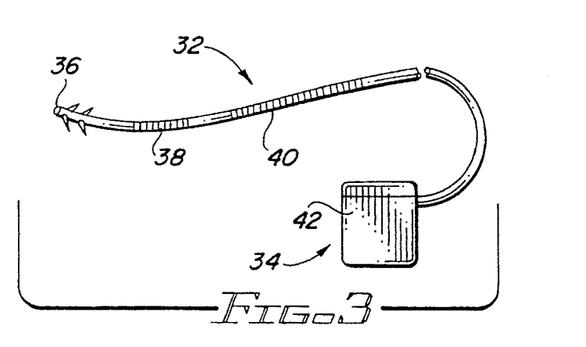
FIG. 3 is a perspective view of a tripolar lead arrangement connected to a cardiac stimulating device.

The effects of post-shock block are somewhat less severe when a tripolar rather than a bipolar lead arrangement is used. As shown in FIG. 3, a tripolar lead 32 may be connected to a cardiac stimulating device 34, in much the same way as a bipolar lead. In contrast to the bipolar arrangement, however, there is no common sense and shock electrode. Sensing (and pacing) is performed between tip electrode 36 and a ring electrode 38, which is the indifferent electrode for pacing and sensing. Shocks are applied with a coil electrode 40 and a can electrode 42. The can electrode 42 is the indifferent shock electrode.

When a defibrillation shock is applied to the patient's heart using the tripolar lead configuration of FIG. 3, current flows primarily between the coil electrode 40 and the can electrode 42. As a result, the capacitances associated with the coil electrode 40 and the can electrode 42 are charged and the electrode/electrolyte interface polarizes. However, because sensing takes place between the tip electrode 36 and the ring electrode 38, which are isolated to some degree from the coil electrode 40 and the can electrode 42, the post shock blocking effect is not as extreme as when a bipolar lead arrangement is used. Nevertheless, the post shock blocking effect is not eliminated, because leakage currents within the device's electronic circuitry will still charge the capacitances associated with the tip electrode 36 and the ring electrode 38.

Moreover, tripolar leads are generally not as attractive as bipolar leads for applying cardioversion and defibrillation shocks. Tripolar leads are inferior to bipolar leads in this respect because, in order to allow for the presence of the ring electrodes, the shocking coils in tripolar leads are shorter than those in bipolar leads and shorter coils have been found to reduce the efficacy with which the coil electrode applies shocks to the heart. The farthest distance along the leads that the coil electrodes in both type of leads may extend is restricted by the size of the heart chamber into which the leads are placed. However, in tripolar leads the coil electrodes must accommodate the ring electrode 38. Thus, the coil electrode 40 in tripolar lead 32 (FIG. 3) cannot extend as far along the lead toward the tip electrode 36 (FIG. 3) as the coil electrode 24 (FIG. 2) can extend toward tip 22 (FIG. 2). Moreover, the construction of a tripolar lead is more complex, due to the presence of an extra electrode and the associate conductor and connections to it in the lead body. In addition, tripolar leads have a larger lead diameter and a stiffer lead body than bipolar leads, due to the presence of the extra conductor and insulating materials.

Thus, for all lead systems it would be desirable to be able to reduce the effects of post shock block. Reducing the effects of post shock block would allow cardiac stimulating devices to monitor a patient's heartbeat signals without becoming obscured by the blocking voltages induced by during the application of conventional cardioversion and defibrillation shocks. In accordance with the present invention, it has been determined that the effects of post shock block can be significantly reduced if the shocks that are applied to the heart are charge-balanced (i.e., contain no net DC component). The experimental set-up shown schematically in FIG. 4 was used to confirm that shocks of this type significantly reduce the effects of post shock block. A tank 44 of normal saline solution was used to represent the blood and heart tissue of a patient. Single 1 V peak-to-peak sine wave cycles of 10 ms in duration were generated at a repetition rate of two pulses per second by voltage source 46. The sine wave cycles produced signals in the saline solution comparable to the normal heartbeat signals that occur in the heart. The signals in the saline solution were monitored using a tip electrode 48 and a coil electrode 50 of a lead 52.

Figure 4:
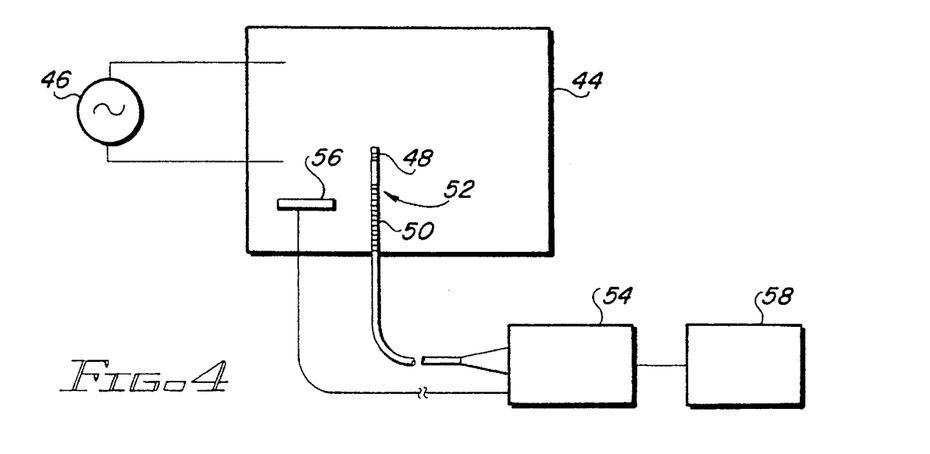
FIG. 4 is a simplified schematic diagram of the experimental arrangement used to determine the magnitude of the post shock block effect for various shock waveforms.

The voltage between the tip electrode 48 and the coil electrode 50 was measured using sensing circuitry 54. The measured voltage was provided to a processing unit 58. When it was desired to simulate the effects of post shock block, a high energy pulse from the pulse generating circuitry 54 was delivered to the saline solution via a metal plate electrode 56 and the coil electrode 50.

In a cardiac stimulating device, pacing pulses are typically applied to the heart through a blocking capacitor that filters out undesirable DC currents. Because pacing pulses typically have magnitudes on the order of several volts, it is feasible to generate pacing pulses directly from the cardiac stimulating device battery using digital switching circuitry. In order to generate cardioversion and defibrillation shocks, however, it is necessary to produce significantly higher voltages (e.g., 50–1000 V). To generate shocks with voltages of this magnitude, cardiac stimulating devices contain a storage capacitor that is charged by the battery when it is desired to apply a shock. Once the storage capacitor is charged to the appropriate level, switching circuitry within the cardiac stimulating device is used to discharge the capacitor through the shock electrodes connected to the heart.

Figure 5:
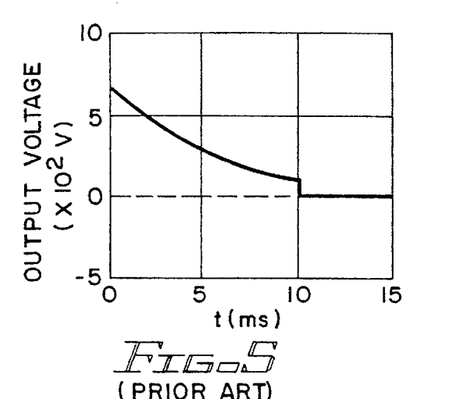
FIG. 5 is a conventional monophasic shock waveform.

A commonly used cardioversion and defibrillation shock waveform is the monophasic shock. A typical monophasic shock waveform is shown in FIG. 5. The monophasic shock of FIG. 5 exhibits an exponential decay. The time constant of the decay is equal to the product of the capacitance of the storage capacitor used to generate the shock and the resistance of the blood and heart tissue though which the capacitor is discharged.

The monophasic shock of FIG. 5 was applied to the saline solution using the set-up of FIG. 4. The resulting voltage measured between the tip electrode 48 and the coil electrode 54 is shown in the top trace of FIG. 6. Whenever the processing unit 58 determined that the voltage between the tip electrode 48 and the coil electrode 50 exceeded a predetermined threshold, the processing unit 58 confirmed that a heartbeat signal was detected. Comparable algorithms are used in typical cardiac stimulating devices to determine whether or not measured signals correspond to cardiac events.

Figure 6:
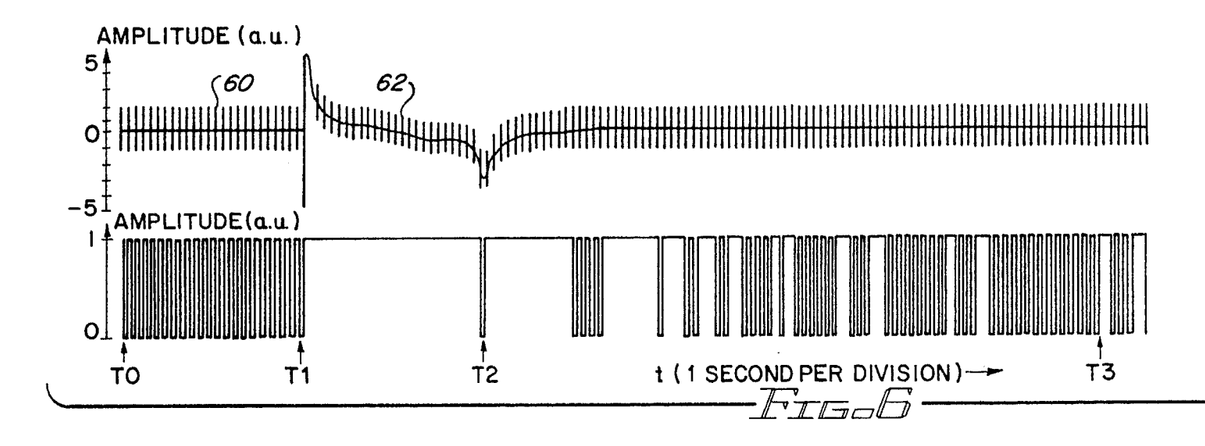
FIG. 6 is a dual trace graph showing the effects of post shock block following the application of the conventional monophasic shock of FIG. 5.

As shown in the upper trace of FIG. 6, during the period from T0 to T1, the peak-to-peak magnitude of the measured heartbeat signals, such as an illustrative heartbeat signal 60, is approximately 3.5 units. The lower trace in FIG. 6 shows how each of these heartbeat signals was successfully detected. At time T1, the monophasic shock of FIG. 5 was applied to the saline solution with the coil electrode 50 and the plate electrode 56 (FIG. 4). The signals subsequently measured between the tip electrode 48 and the coil electrode 50, such as illustrative heartbeat signal 62, have a reduced magnitude (of approximately 2–2.5 units), and are therefore not detected by the processing circuitry 58, as shown in the lower trace of FIG. 6. Although a heartbeat signal is successfully detected at time T2 (nine seconds after the shock was applied), considerable undersensing of the heartbeat signals persists long after the shock was applied. For example, at T3, well over 30 seconds after the shock was applied, a heartbeat signal was not properly detected.

Figure 7:
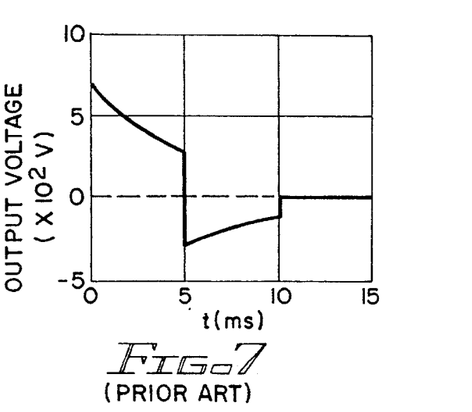
FIG. 7 is a conventional equal-phase duration biphasic shock waveform.
Figure 8:
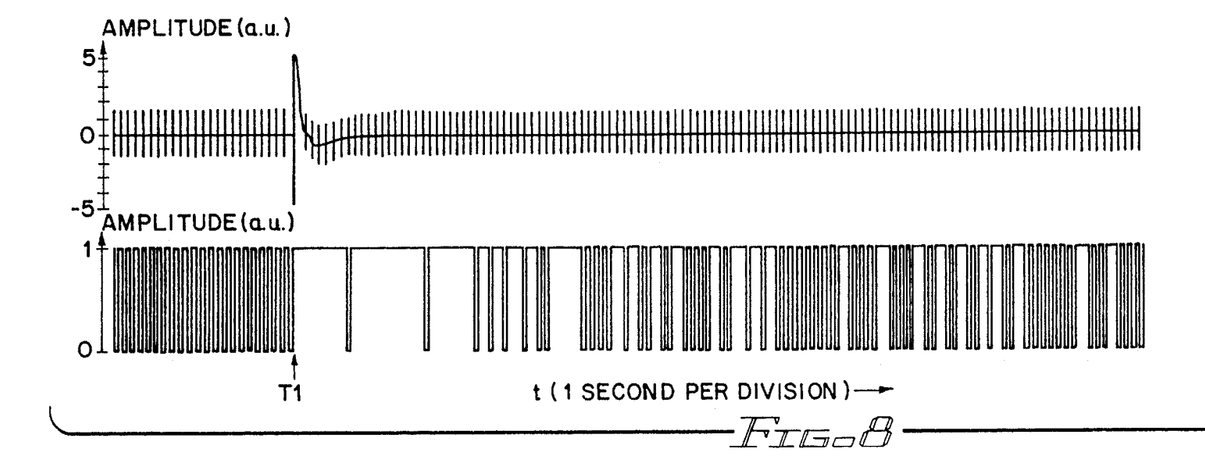
FIG. 8 is a dual trace graph showing the effects of post shock block following the application of the conventional equal-phase biphasic shock of FIG. 7.

Similar results were obtained when the conventional equal-phase duration biphasic shock of FIG. 7 was applied. As shown in FIG. 8, after the biphasic shock of FIG. 7 was applied at time T1, the heartbeat signals were significantly undersensed for at least 30 seconds due to the effects of post shock block. Thus, as shown in FIGS. 6 and 8, conventional monophasic and biphasic shocks create substantial post shock block effects that interfere with the ability of the processing unit 58 to detect the heartbeat signals.

Figure 9:
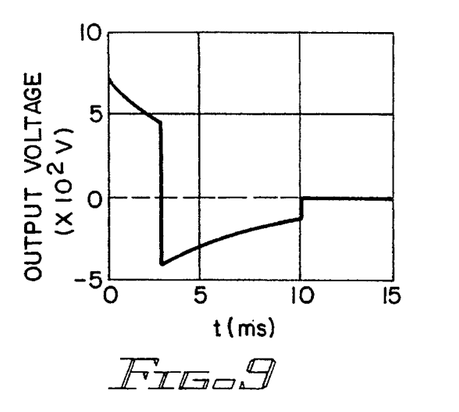
FIG. 9 is an illustrative biphasic charge-balanced shock waveform.

In contrast, when charge-balanced shocks are used, the effects of post shock block are substantially reduced. A biphasic charge-balanced shock waveform suitable for use as a cardioversion or defibrillation shock is shown in FIG. 9. The shock of FIG. 9 is called a "charge-balanced" shock, because the time-integrated current applied to the heart during the positive phase of the shock (t=0 ms to approximately t=3 ms) is equal in magnitude to the time-integrated current applied to the heart during the negative phase of the shock (approximately t=3 ms to t=10 ms). Thus the charge delivered to the blood and tissue by the tip electrode 48 (FIG. 4) during the positive phase is balanced by the charge removed from this area during the negative phase of the shock. By balancing the charge delivered through the electrodes, the polarization of the electrode/electrolyte interface—which is the cause of post shock block—is significantly reduced.

Any suitable arrangement for applying charge-balanced shocks to the heart may be used. One convenient approach for generating a charge-balanced shock is to apply the shock to the heart from a charged storage capacitor. With this approach, the shock will exhibit the same characteristic exponential decay exhibited by the conventional shocks of FIGS. 5 and 7. For charge-balanced biphasic shocks of the type shown in FIG. 9, a good approximation of the current during the positive and negative phases of the shock is given by Equation 1.

$$\text{Shock\_Current} = \begin{array}{ll} +(V_0/R)\,e^{-t/RC} & 0 < t < t_1 - \\ -(V_0/R)\,e^{-t/RC} & t_1 < t < t_2 \\ 0 & \text{elsewhere} \end{array} \quad (1)$$

The resistance of the blood and heart tissue through which the shock is delivered is R. The storage capacitor used to deliver the shock has a capacitance of C. The initial voltage across the capacitor is $V_0$. In Equation 1, t represents time. The duration of the positive shock phase is $t_1$. The total duration of the shock is $t_2$. From t=0 (the beginning of the shock) to $t_1$, Shock_Current is positive. From $t_1$ to $t_2$, Shock_Current is negative. From Equation 1 it follows that the magnitude of the time-integrated current for the positive phase of the shock is given by Equation 2.

$$\text{Pos\_Time\_Integrated\_Current} = \frac{V_0}{R}\int_0^{t_1} e^{-t/RC}dt \quad (2)$$

Performing the integration in Equation 2 one obtains the relationship in Equation 3.

$$\text{Pos\_Time\_Integrated\_Current} = V_0 C(1-e^{-t_1/RC}) \quad (3)$$

The magnitude of the time-integrated current for the negative phase of the shock is given by Equation 4.

$$\text{Neg\_Time\_Integrated\_Current} = \frac{V_0}{R}\int_{t_1}^{t_2} e^{-t/RC}dt \quad (4)$$

Carrying out the integration in Equation 4 results in the expression of Equation 5.

$$\text{Neg\_Time\_Integrated\_Current} = V_0 C(e^{-t_1/RC} - e^{-t_2/RC}) \quad (5)$$

For charge-balanced biphasic shocks, the magnitude of the time-integrated current of the positive shock phase is equal to the magnitude of the time-integrated current of the negative shock phase. Equations 3 and 5 can therefore be equated to one another and the resulting expression solved for the duration of the positive shock phase ($t_1$) as a function of the total shock duration ($t_2$), as shown in Equation 6.

$$t_1 = RC\,\ln[2/(1+e^{(-t_2/RC)})] \quad (6)$$

For a chosen total shock duration (e.g., 10 ms), Equation 6 can be used to determine the duration of the first (positive) phase to ensure that the shock is charge-balanced, as a function of the resistance of the patient's blood and heart tissue and the capacitance of the cardiac stimulating device storage capacitor. In addition to using Equation 6 to select appropriate relative durations for the positive and negative shock phases, a value for the initial shock voltage, $V_0$, must be selected (see Equation 1). The voltage $V_0$ is preferably selected using conventional methods for determining the appropriate value for the strength of cardioversion and defibrillation shocks.

Figure 10:
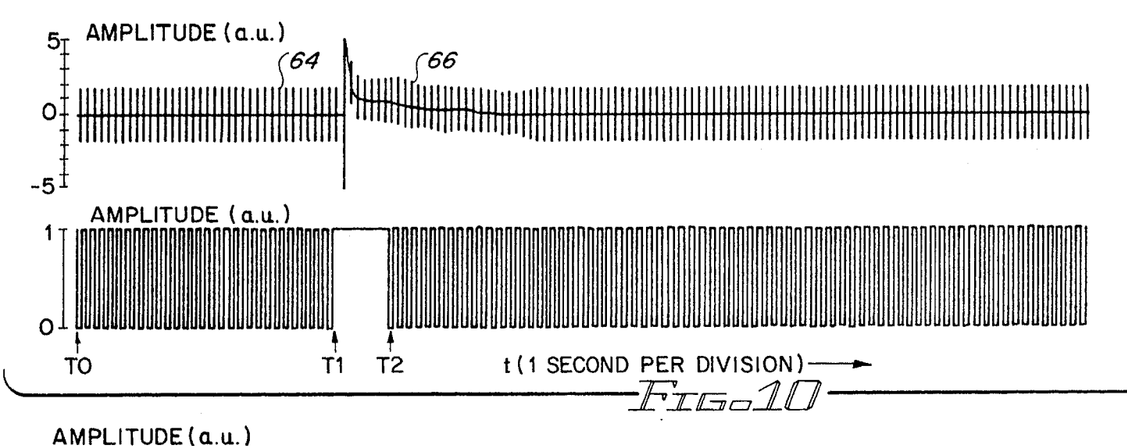
FIG. 10 is a dual trace graph showing the effects of post shock block following the application of the biphasic charge-balanced shock of FIG. 9.

The magnitude of the post shock block effect produced by the charge-balanced biphasic shock of FIG. 9 was evaluated using the system of FIG. 4. As shown in the upper trace in FIG. 10, during the period from T0 to T1, the peak-to-peak magnitude of the measured heartbeat signals, such as an illustrative heartbeat signal 64, is approximately 3.5 units. The lower trace in FIG. 10 shows how each of these heartbeat signals was successfully detected. At time T1, the charge-balanced biphasic shock of FIG. 9 was applied to the saline solution with the coil electrode 50 and the plate electrode 56 (FIG. 4). At time T2, less than three seconds after the charge-balanced shock was applied, the heartbeat signals measured between the tip electrode 48 and the coil electrode 50, such as heartbeat signal 66, were of sufficient magnitude (approximately 3.5 units) to be successfully detected by the processing unit 58 (FIG. 4). Thus, as shown on the lower trace in FIG. 10, the only interruption in the detection of heartbeat signals was the period from T1 to T2, a delay of less than three seconds.

Figure 11:
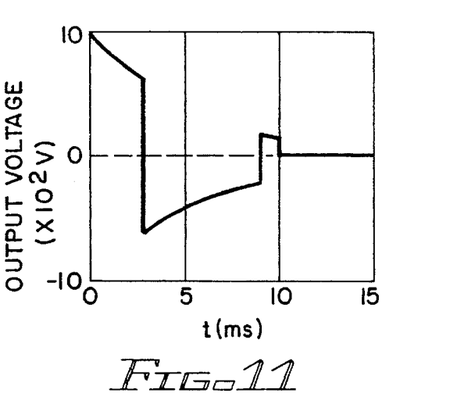
FIG. 11 is an illustrative triphasic charge-balanced shock waveform.

Significant reductions in post shock block were also accomplished using the triphasic charge-balanced shock shown in FIG. 11. The charge-balanced shock of FIG. 11 is made up of three phases: a positive phase from approximately 0 ms to 2.7 ms, a negative phase from approximately 2.7 ms to 6.3 ms, and a positive phase from 6.3 ms to 10 ms. The triphasic shock of FIG. 11 is charge-balanced because the time-integrated current applied to the heart during the two positive phases of the shock is equal in magnitude to the time-integrated current applied to the heart during the negative phase of the shock.

A suitable approach for generating a charge-balanced triphasic shock is to apply the shock to the heart from a charged storage capacitor. The triphasic shock will thus exhibit the characteristic exponential decay of a capacitor discharging through a the resistance, as shown in FIG. 11. For triphasic shocks of the type shown in FIG. 11, a good approximation of the current during the two positive phases and one negative phase of the shock is given by Equation 7.

$$\text{Shock\_Current} = \begin{array}{ll} + (V_0/R) e^{-t/RC} & 0 < t < t_1 \\ \phantom{+} (V_0/R) e^{-t/RC} & t_1 < t < t_2 \\ + (V_0/R) e^{-t/RC} & t_2 < t < t_3 \\ \phantom{+} 0 & \text{elsewhere} \end{array} \quad (7)$$

The resistance of the heart tissue and blood through which the shock is delivered is R. The storage capacitor used to deliver the shock has a capacitance of C. The initial voltage across the capacitor is $V_0$. The duration of the first positive shock phase is $t_1$. From t=0 (the beginning of the shock) to $t_1$, Shock_Current is positive. The negative shock phase begins at $t_1$ and ends at $t_2$, so that from $t_1$ to $t_2$, Shock_Current is negative. The second positive shock phase begins at $t_2$ and ends at $t_3$. During the second positive shock phase Shock_Current is positive. From Equation 7 it follows that the magnitude of the time-integrated current for the first positive phase of the shock is given by Equation 8.

$$\text{First\_Pos\_Time\_Integrated\_Current} = \frac{V_0}{R} \int_0^{t_1} e^{-t/RC} dt \quad (8)$$

Performing the integration in Equation 8 one obtains the relationship in Equation 9.

$$\text{First\_Pos\_Time\_Integrated\_Current} = V_0 C(1 - e^{-t_1/RC}) \quad (9)$$

The magnitude of the time-integrated current for the negative phase of the shock is given by Equation 10.

$$\text{Neg\_Time\_Integrated\_Current} = \frac{V_0}{R} \int_{t_1}^{t_2} e^{-t/RC} dt \quad (10)$$

Carrying out the integration in Equation 10 results in the expression of Equation 11.

$$\text{Neg\_Time\_Integrated\_Current} = V0C(e^{-t_1}/RC - e^{-t_2/RC}) \quad (11)$$

The magnitude of the time-integrated current for the second positive phase of the shock is given by Equation 12.

$$\text{Second\_Pos\_Time\_Integrated\_Current} = \frac{V_0}{R} \int_{t_2}^{t_3} e^{-t/RC} dt \quad (12)$$

Carrying out the integration in Equation 12 results in the expression of Equation 13.

$$\text{Second\_Pos\_Time\_Integrated\_Current} = V0C(e^{-t_2}/RCe^{-t_3/RC}) \quad (13)$$

For the triphasic charge-balanced shock of FIG. 11, the total magnitude of the time-integrated currents of the first and second positive shock phases is equal to the magnitude of the time-integrated current of the negative shock phase. This relationship is shown in Equation 14.

$$\text{First\_Pos\_Time\_Integrated\_Current} + \text{Second\_Pos\_Time\_Integrated\_Current} = \text{Neg\_Time\_Integrated\_Current} \quad (14)$$

Substituting Equations 9, 11, and 13 into Equation 14, it can be determined which relationships between the first second, and third phases will result in charge-balanced triphasic shocks. Solving Equation 14 for $t_2$, one obtains Equation 15.

$$t_2 = RC \ln[2/\{2e^{(-t_1/RC)} + e^{(-t_3/RC)} - 1\}] \quad (15)$$

For given values of $t_3$ (the total shock duration) and $t_1$ (the duration of the first positive pulse), Equation 15 can be used to determine a suitable value of $t_2$ to ensure that the shock of FIG. 11 is charge-balanced. The duration of the negative phase is $t_2-t_1$. If Equation 15 is solved for $t_1$, values of $t_3$ and $t_2$ can be used to determine the appropriate value of $t_1$ to ensure that the triphasic shock of FIG. 11 is charge-balanced.

Figure 12:
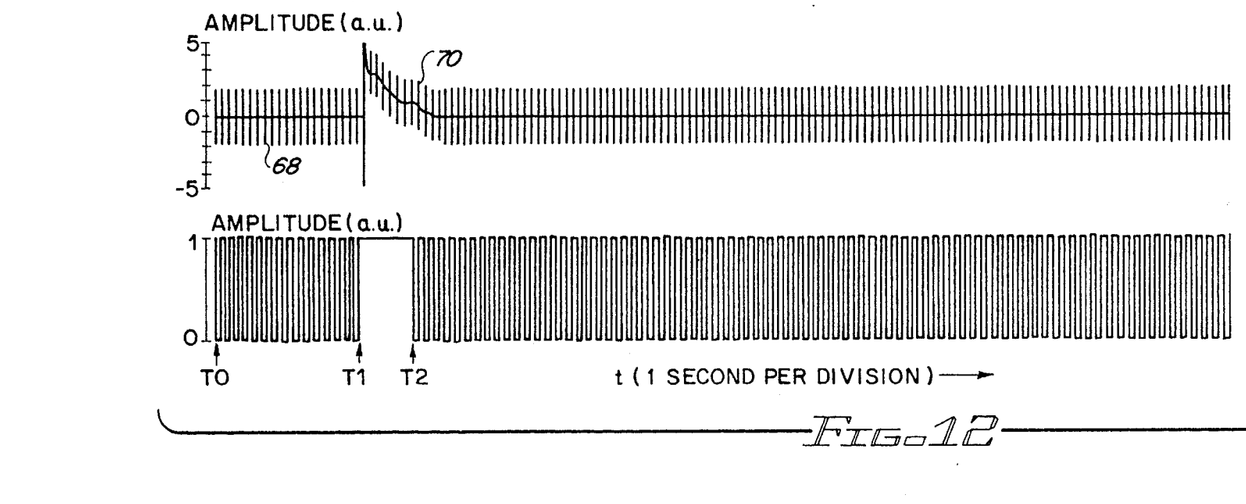
FIG. 12 is a dual trace graph showing the effects of post shock block following the application of the triphasic charge-balanced shock of FIG. 11.

The magnitude of the post shock block effect produced by the charge-balanced triphasic shock of FIG. 11 was evaluated using the same experimental setup (FIG. 4) that was used to evaluate the charge-balanced biphasic shock waveform of FIG. 9 As shown in the upper trace in FIG. 12, during the period from T0 to T1, the peak-to-peak magnitude of the measured heartbeat signals, such as an illustrative heartbeat signal 68, is approximately 3.5 units. The lower trace in FIG. 12 shows how each of these heartbeat signals was successfully detected. At time T1, the charge-balanced triphasic shock of FIG. 11 was applied to the saline solution with the coil electrode 50 and the plate electrode 56 (FIG. 4). At time T2, less than three seconds after the charge-balanced shock was applied, heartbeat signals measured between the tip electrode 48 and the coil electrode 50, such as heartbeat signal 70, were of sufficient magnitude (approximately 3.5 units) to be successfully detected by the processing unit 58 (FIG. 4).

Thus, the biphasic charge-balanced shock of FIG. 9 and the triphasic charge-balanced shock of FIG. 11 both significantly reduced the effects of post shock block relative to the effects exhibited when the conventional shocks of FIGS. 5 and 7 were used. If desired, charge-balanced shocks with a greater number of phases can also be used. However, the total length of the charge-balanced shock preferably should remain less than approximately 10 ms. It has been shown empirically that shocks of this duration are effective at terminating arrhythmia episodes at low energy levels. It is also preferable that each phase be at least approximately 2–3 ms in duration. Pulses significantly shorter than 2 ms will not be as effective as longer pulses at terminating arrhythmias, because the heart behaves as a low-pass filter, attenuating short pulses.

The efficacy of charge-balanced shocks in terminating arrhythmias was evaluated using a canine model implanted with a transvenous defibrillation system. In the first phase, an electrode in the right ventricle was used as the cathode and an electrode in the superior vena cava commoned to a subcutaneous patch was used as the cathode. The triphasic charge-balanced waveform exhibited defibrillation characteristics comparable or superior to those of a conventional biphasic shock. For the chosen durations, defibrillation thresholds were found to be somewhat higher using the charge-balanced biphasic shock. The measured defibrillation thresholds for a conventional biphasic shock and for illustrative biphasic and triphasic charge-balanced shocks are shown in Table 1.

TABLE 1

| Waveform | DFT(J) | DFT + (J) | E50(J) |
|---|---|---|---|
| Conventional Biphasic (4/4 ms) | 5.0 | 5.0 | 4.7 |
| Charge Balanced Biphasic (4/7 ms) | 9.0 | 9.0 | 7.7 |
| Charge Balanced Triphasic (3.3/6.3/1.4 ms) | 4.0 | 7.0 | 4.3 |

Defibrillation thresholds were evaluated using three separate criteria. The DFT threshold is the threshold obtained by using a binary tree search pattern to determine the minimum energy necessary to defibrillate. For example, if an initial defibrillation energy of 16 J results in a successful defibrillation, then a pulse energy of 8 J (16/2) is used in the next defibrillation attempt. If the 8 J pulse fails to defibrillate, then the pulse energy is increased, to 12 J ((16+8)/2). If the 12 J pulse is successful, a defibrillation energy of 10 J ((8+12)/2) is used next. This process is continued until the desired level of accuracy is obtained. The resulting DFT threshold is the minimum energy found to be successful at terminating a fibrillation episode. The DFT+threshold is similar to the threshold DFT, but further requires a second successful application of the shock at the same energy. The E50 threshold is a weighted average of the shock energy at the last three "reversals." Reversals are the points at which failed attempts at defibrillation are followed by successful attempts and when successful attempts are followed by failures.

As shown in Table 1, the defibrillation thresholds for these particular durations for the charge-balanced biphasic shock are somewhat higher than those of the conventional biphasic shock. The defibrillation thresholds for the triphasic charge-balanced shock are comparable or superior to the thresholds for the conventional shock. Thus, charge-balanced shocks, particularly the triphasic shock, are suitable for defibrillation purposes, while being superior to conventional shocks with respect to the effects of post shock block.

Another advantage of using charge-balanced shocks is that electrolytic corrosion of the electrodes is reduced. Portions of the leads, such as the crimp connections between the electrodes, the internal conductors in the leads, and the electrodes, are exposed to ions in the blood and tissue of the patient. When cardioversion and defibrillation shocks are applied, the current of the shocks will produce electrolytic corrosion at the portion of the leads exposed to the ions. With a charge-balanced shock waveform, however, there is no net delivery of current. As a result, shock-induced electrolytic corrosion is minimized.

Figure 13:
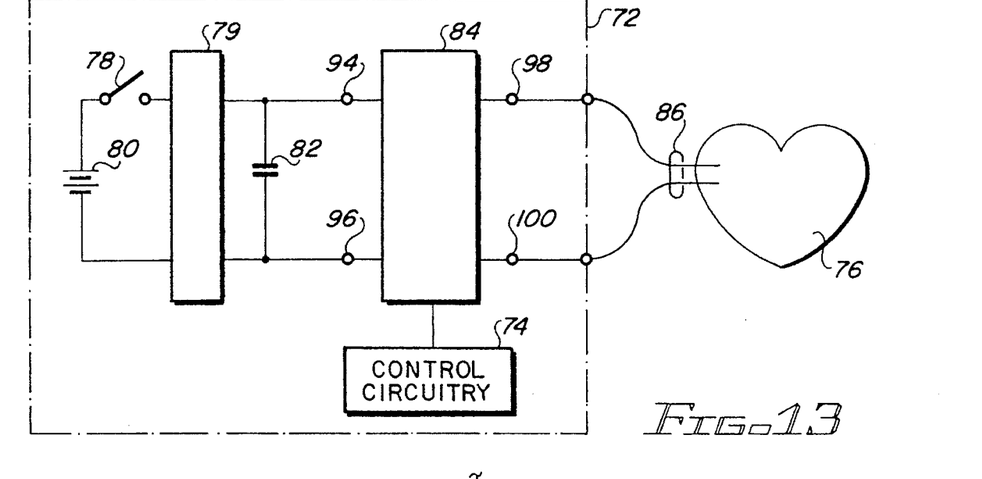
FIG. 13 is an illustrative cardiac stimulating device with which charge-balanced antiarrhythmia shocks can be applied to the heart.

Charge-balanced waveforms, such as those shown in FIGS. 9 and 11, can be applied to a patient's heart using the cardiac stimulating device arrangement shown in FIG. 13. A cardiac stimulating device 72 contains control circuitry 74, which is capable of executing instructions to implement various control routines. When it is determined that a shock is to be applied to a patient's heart 76, the control circuitry 74 closes a switch 78 so that a battery 80 powers the voltage boosting circuitry 79 that charges a capacitor 82. After the capacitor 82 has been charged sufficiently to deliver a shock of a desired energy level, the switch 78 is opened and the shock is applied to the heart 76 via switching circuitry 84 and a lead 86. Any suitable lead arrangement can be used. For example, lead 86 may be a bipolar or tripolar lead. The indifferent shock electrode may be the can of the cardiac stimulating device, a subcutaneous patch, or an electrode implanted, e.g., in the superior vena cava. A lead arrangement in which the shock electrodes are positioned at a remote location relative to the sense electrodes can also be used.

The control circuitry 74 is preferably capable of executing instructions to implement routines that determine the polarity of the applied shock. Thus, when appropriate during the application of the shock, the control circuitry 74 directs the switching circuitry 84 to reverse the polarity of the applied shock to ensure that the shock is charge-balanced.

Figure 14:
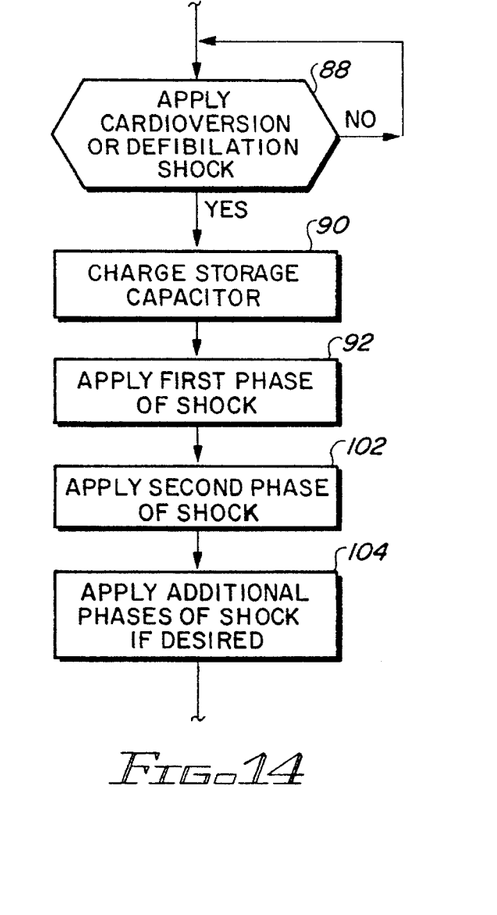
FIG. 14 is a flow chart depicting an illustrative process for applying the positive and negative phases of a charge-balanced shock to the heart.

As shown in FIG. 14, if the control circuitry 74 (FIG. 13) determines at test 88 that a cardioversion or defibrillation shock should be applied to the patient's heart (FIG. 13), then at step 90 the switch 78 (FIG. 13) is closed, causing the battery 80 (FIG. 13) to power the voltage boosting circuitry and, in turn, charge the capacitor 82 (FIG. 13). When the capacitor 82 (FIG. 13) has been charged sufficiently, the switch 78 (FIG. 13) is opened. At step 92 the cardiac stimulating device (FIG. 13) applies a first phase of the shock to the heart 76 (FIG. 13). The polarity of the applied shock is determined by the switching circuitry 84 (FIG. 13). Preferably, the switching circuitry 84 (FIG. 13) contains suitable conventional circuitry for reversing the polarity of the shock voltage that is passed from input terminals 94 and 96 (FIG. 13) to output terminals 98 and 100 (FIG. 13), without affecting the magnitude of the shock voltage. At step 102, the cardiac stimulating device 72 (FIG. 13) applies a second phase of the shock to the heart 76 (FIG. 13) for a predetermined interval. The second phase of the shock is opposite in polarity to the first phase of the shock.

If a biphasic charge-balanced waveform is desired, then the cardiac stimulating device 72 (FIG. 13) applies the second phase of the shock for an interval of time sufficient to balance the time-integrated current applied to the heart during the first phase. If a charge-balanced waveform having three or more alternating positive and negative phases is desired, then the cardiac stimulating device 72 (FIG. 13) applies additional phases of the shock waveform at step 104. When the charge-balanced shock is made up of three or more alternating phases, the cardiac stimulating device 72

(FIG. 13) applies the positive and negative phases for appropriate intervals of time to balance the time-integrated current applied to the heart during the positive and negative phases.

Thus methods and apparatus for applying charge-balanced shocks to a patient's heart are provided. One skilled in the art will appreciate that the present invention can be practiced by other than the described embodiments, which are presented for the purposes of illustration and not of limitation, and the present invention is limited only by the claims that follow.

What is claimed is:

1. Apparatus for applying a charge-balanced antiarrhythmia shock to the heart of a patient to reduce the effects of post shock block, comprising:

means for applying at least one positive shock phase to the heart, said positive shock phase having a positive shock phase current; and means for applying at least one negative shock phase to the heart, said negative shock phase having a negative shock phase current, wherein the time-integrated positive shock phase current substantially equals the time-integrated negative shock phase current, and further wherein each shock phase is a portion of a single exponential decay waveform.

2. The apparatus defined in claim 1, wherein:

said means for applying said at least one positive shock phase applies a single positive shock phase; and said means for applying said at least one negative shock phase applies a single negative shock phase.

3. The apparatus defined in claim 1, wherein said means for applying said positive and negative shock phases apply initial and final shock phases of one polarity and an intermediate shock phase of opposite polarity to said one polarity.

4. The apparatus defined in claim 1, comprising:

a capacitor charged to a predetermined voltage; and switching circuitry for applying the voltage across the capacitor to the heart with an alternating polarity.

5. A method for applying a charge-balanced antiarrhythmia shock to the heart of a patient to reduce the effects of post shock block, comprising the steps of:

applying at least one positive shock phase to the heart, said at least one positive shock phase having a positive shock phase current; and applying at least one negative shock phase to the heart, said at least one negative shock phase having a negative shock phase current, wherein the time-integrated positive shock phase current substantially equals the time-integrated negative shock phase current, and further wherein each shock phase is a portion of a single exponential decay waveform.

6. The method defined in claim 5, wherein the steps of applying the positive and negative shock phases to the heart comprise the steps of:

applying a single positive shock phase; and applying a single negative shock phase.

7. The method defined in claim 5, wherein the steps of applying the positive and negative shock phases to the heart comprise the steps of:

applying initial and final shock phases of one polarity; and applying an intermediate shock phase of opposite polarity to said one polarity.

8. The method defined in claim 5, comprising the steps of:

charging a capacitor; and using switching circuitry to apply the voltage across the capacitor to the heart with alternating polarity.

9. A cardiac stimulating device for applying a charge-balanced antiarrhythmia shock to the heart of a patient to reduce the effects of post shock block, comprising:

a battery;

a capacitor;

means for charging said capacitor with said battery when it is desired to apply said charge-balanced antiarrhythmia shock to the heart;

means for applying at least one positive shock phase to the heart from said capacitor, said at least one positive shock phase having a positive shock phase current; and means for applying at least one negative shock phase to the heart from said capacitor, said at least one negative shock phase having a negative shock phase current, wherein the time-integrated positive shock phase current substantially equals the time-integrated negative shock phase current, and further wherein each shock phase is a portion of a single exponential decay waveform.

10. The cardiac stimulating device defined in claim 9, wherein:

said means for applying said at least one positive shock phase applies a single positive shock phase; and said means for applying said at least one negative shock phase applies a single negative shock phase.

11. The cardiac stimulating device defined in claim 9, wherein said means for applying the positive and negative shock phases apply initial and final shock phases of one polarity and an intermediate shock phase of opposite polarity to said one polarity.

12. The cardiac stimulating device defined in claim 9, wherein the means for applying the positive and negative shock phases comprise a bipolar lead.

13. The cardiac stimulating device defined in claim 9, wherein the means for applying the positive and negative shock phases comprise a tripolar lead.

* * * * *